United States Patent
Sadoff et al.

(10) Patent No.: US 8,658,136 B2
(45) Date of Patent: Feb. 25, 2014

(54) METHODS TO INCREASE TRANSGENE EXPRESSION FROM BACTERIAL-BASED DELIVERY SYSTEMS BY CO-EXPRESSING SUPPRESSORS OF THE EUKARYOTIC TYPE I INTERFERON RESPONSE

(71) Applicant: Aeras Global TB Vaccine Foundation, Bethesda, MD (US)

(72) Inventors: Jerald C. Sadoff, Washington, DC (US); Mohamad F. Jamiluddin, Frederick, MD (US); Ravi P. Anantha, Gaithersburg, MD (US); John F. Fulkerson, Jr., Silver Springs, MD (US)

(73) Assignee: Aeras Global TB Vaccine Foundation, Bethesda, MD (US)

( * ) Notice: Subject to any disclaimer, the term of this patent is extended or adjusted under 35 U.S.C. 154(b) by 0 days.

(21) Appl. No.: 13/858,289

(22) Filed: Apr. 8, 2013

(65) Prior Publication Data
US 2013/0224242 A1    Aug. 29, 2013

Related U.S. Application Data

(62) Division of application No. 12/964,830, filed on Dec. 10, 2010, now Pat. No. 8,414,884, which is a division of application No. 12/558,137, filed on Sep. 11, 2009, now Pat. No. 7,883,696, which is a division of application No. 11/854,027, filed on Sep. 12, 2007, now Pat. No. 7,608,256.

(51) Int. Cl.
*A61K 49/00* (2006.01)
*A61K 39/02* (2006.01)
*A61K 39/112* (2006.01)

(52) U.S. Cl.
USPC ....... 424/9.2; 424/9.1; 424/184.1; 424/200.1; 424/234.1; 424/258.1

(58) Field of Classification Search
None
See application file for complete search history.

(56) References Cited

U.S. PATENT DOCUMENTS

| 6,525,029 | B1 | 2/2003 | Falck-Pedersen et al. |
| 7,608,256 | B2 | 10/2009 | Sadoff et al. |
| 2004/0077090 | A1 | 4/2004 | Short |
| 2007/0160609 | A1 | 7/2007 | Maroun |
| 2007/0207526 | A1 | 9/2007 | Coit |

FOREIGN PATENT DOCUMENTS

JP    2001521743    11/2001

OTHER PUBLICATIONS

Kotton, C. et al., "Enteric pathogens as vaccine vectors for foreign antigen delivery", Infection and Immunity, 2004, 72(10): 5535-5547.
Saba, P. et al., "Engineering bacterial vectors for delivery of genes and proteins to antigen-presenting cells", Molecular Pharmaceuticals, 2007, 14(1):4-17.
Liang, G. et al., "A universal cloning vector using vaccinia topoisomerase I", Molecular Biotechnology, 2006, 33(1):23-28.

*Primary Examiner* — Rodney P. Swartz
(74) *Attorney, Agent, or Firm* — Pepper Hamilton LLP

(57) ABSTRACT

Bacterial delivery systems with improved transgene expression are provided. The recombinant bacterial delivery systems deliver transgenes of interest and suppressors of the eukaryotic Type I interferon response to eukaryotic cells. Suppression of the eukaryotic Type I interferon response allows improved expression of the encoded transgene.

16 Claims, 3 Drawing Sheets

METHODS TO INCREASE TRANSGENE EXPRESSION FROM BACTERIAL-BASED DELIVERY SYSTEMS BY CO-EXPRESSING SUPPRESSORS OF THE EUKARYOTIC TYPE I INTERFERON RESPONSE

BACKGROUND OF THE INVENTION

1. Field of the Invention

The invention generally relates to bacterial delivery systems that promote improved transgene expression in eukaryotic cells by inhibiting the innate type I interferon response. In particular, the invention provides recombinant bacterial delivery systems that deliver to eukaryotic cells: i) transgenes and ii) suppressors of the eukaryotic Type I interferon response.

2. Background of the Invention

Live attenuated mutants of several pathogenic bacteria have been exploited as potential vaccine vectors for heterologous antigen delivery by the mucosal route. Such live vectors offer the advantage of targeted delivery of macromolecules to mammalian cells and tissues in a single oral, intranasal or inhalational dose, thereby stimulating both systemic and mucosal immune responses. The great potential of bacteria-mediated transfer of plasmid DNA encoding vaccine antigens and/or therapeutic molecules has been demonstrated in experimental animal models of infectious diseases, tumors and gene deficiencies.

Unfortunately, bacterial vectored discharge of passenger RNA/DNA and other molecules for the expression of foreign proteins or inhibitory RNAs in mammalian cells results in a type I interferon (IFN) response. A central component of the host's surveillance system for invading pathogens is an evolutionarily conserved family of pathogen recognition receptors (PRR) which bind patterned microbial/viral ligands ranging from cell wall components to nucleic acids. PRR signaling results in the activation of transcription factors such as Nuclear Factor-B (NF-B) and interferon regulatory factor 3 (IRF-3), which provide the inflammatory context for the rapid activation of host defenses. The NF-B pathway controls the expression of proinflammatory cytokines such as IL-1 and tumor necrosis factor-α, whereas the IRF-3 pathway leads to the production of type I interferons (IFN-α and IFN-β). This initially produced "first wave" IFN triggers expression of a related factor, IRF-7, which is normally present in most cells at very low concentrations (Sato M et al., Immunity, 13(4) 539-548; 2000). IRF-3 most likely cooperates with IRF-7 and is responsible for a positive feed back loop that initiates the synthesis of several IFN-α subtypes as the "second wave" IFNs (Marie et al., EMBO J. 17(22), 6660-6669; 1998 and Sato M et al., FEBS Lett 441(1)106-110; 1998.). Type I IFNs activate several hundred IFN stimulated genes by autocrine and paracrine signaling (ISGs) (de Veer et al., J Leukocyte Biol 69(6) 912-920, 2001; Der et al., Proc. Natl. Acad. Sci. USA 95(26) 15623-15628; 1998), some of which code for antiviral proteins. To date, three IFN stimulated pathways have been firmly established. These include protein kinase R (PKR) (Williams Oncogene 18(45) 6112-6120; 1999), the 2'-5' oligoadenylate-synthetase (2'-5' OAS) (Silverman., J Interferon Res 14(3) 101-104; 1994) and the Mx proteins (Haller and Kochs Traffic 3(10) 710-714; 2002). This type I IFN response limits the expression of foreign genes or inhibitory RNAs by means of PKR and 2'-5' OAS. Activated PKR blocks translation by phosphorylating the a subunit of eukaryotic initiation factor eIF2. On the other hand, 2-5A synthetases produce short, 2'-5' OAS associated oligoadenylates which activate RNase L, a single-stranded specific endoribonuclease that digests mRNA and ribosomal RNA. The importance of the Mx protein in host survival following infection with certain RNA viruses has been amply demonstrated (Hefti et al., J Virology 73(8) 6984-6991; 1999) but the exact mode of action is still unknown. This type I IFN response thus limits the expression of foreign nucleic acids by mechanisms which reduce RNA production and stability and also inhibits translation of message from passenger nucleic acids delivered by a bacterial vector.

Various components of bacterial vectors elicit the IFN response in host cells. The bacterium itself can trigger an IFN response through Toll-like receptors. Double stranded RNA produced by passenger nucleic acids during transcription not only induces type I IFNs but also directly activates PKR and 2'-5' OAS. Plasmid DNA, upon its delivery into the cytoplasm of mammalian cells, often contains cryptic promoters that generate anti-sense RNA which anneals with mRNA to form dsRNA. All these components of bacterial vectors thus diminish the efficacy of bacterial vectors as biomedical tools.

U.S. Pat. No. 6,525,029 (Falck-Perersen et al., Feb. 25, 2003) describes methods of inhibiting an immune response to a recombinant vector such as an adenoviral vector. However, this technology is directed toward preventing humoral (e.g. antibody) responses to long-term expression of genes encoded by a vector and clearance of the vector by the immune system, and does not address prevention of a type I IFN response to a bacterial vector or its passenger nucleic acids.

The prior art has thus-far failed to provide bacterial vectors that eliminate or attenuate the type I IFN response of host cells.

SUMMARY OF THE INVENTION

The present invention provides recombinant bacterial expression vectors that successfully eliminate or attenuate the type I IFN response that is usually mounted by mammalian host cells in response to invasion by a bacterial expression vector. The recombinant bacterial expression vectors circumvent the usual IFN response by encoding factors that inhibit or suppress the type I IFN response in host cells. The IFN suppressor is expressed either i) in the bacterial cell for delivery as a protein or ii) in the eukaryotic cell from a nucleotide sequence that is delivered by the bacterial cell. Inhibition of the IFN response allows more robust expression of passenger genes delivered by the bacterial vector, and expression is enhanced only in a eukaryotic cell in which the type I IFN response has been suppressed. For example, when the recombinant bacterial expression vector of the invention delivers passenger nucleotide sequences encoding antigens to which an immune response is desired, production of those antigens by the mammalian cell is not impeded by the host IFN system, the antigens are expressed, and the desired immune response to the antigens may be produced.

It is an object of this invention to provide a genetically engineered bacterium, comprising nucleic acid sequences encoding i) one or more passenger genes; and ii) one or more factors that inhibit a mammalian interferon response. The nucleic acid sequences encoding the one or more passenger genes are operably linked to a eukaryotic promoter, and the nucleic acid sequences encoding the one or more factors that inhibit a mammalian type I interferon response are operably linked to a eukaryotic promoter or a prokaryotic promoter. In yet another embodiment, the expressible nucleic acid sequences encoding the one or more factors that inhibit a mammalian interferon response are present on a chromosome of the genetically engineered bacterium. In further embodiments, one or both of the: i) nucleic acid sequences encoding said one or more passenger genes, wherein the nucleic acid sequences are expressible in a eukaryotic cell; and ii) nucleic acid sequences encoding said one or more factors that inhibit a mammalian interferon response, are present on a plasmid. In addition, the one or more factors that inhibit a mammalian interferon response may be of viral origin. In some embodiments, the one or more passenger genes encode tuberculosis antigens. In further embodiments, the genetically engineered bacterium is a *shigella* bacterium or a *mycobacterium*. Further, the passenger genes may be heterologous transgenes.

The invention further provides a method of increasing the production of one or more gene products of interest in a cell or tissue. The method comprises the step of administering to the cell or tissue a genetically engineered bacterium comprising nucleic acid sequences encoding: i) the one or more gene products of interest and ii) one or more factors that inhibit a mammalian interferon response. The nucleic acid sequences encoding the one or more passenger genes are operably linked to a eukaryotic promoter, and the nucleic acid sequences encoding the one or more factors that inhibit a mammalian type I interferon response are operably linked to a eukaryotic promoter or a prokaryotic promoter. The step of administering is carried out under conditions which allow the genetically engineered bacterium to invade the cell or tissue, and to produce the one or more gene products of interest and the one or more factors within the cell or tissue. In one embodiment, transcription of the expressible nucleic acid sequences is controlled by eukaryotic promoters. In another embodiment, transcription of the expressible nucleic acid sequences encoding the one or more factors that inhibit a mammalian interferon response is controlled by prokaryotic promoters. In yet another embodiment, the expressible nucleic acid sequences encoding the one or more factors that inhibit a mammalian interferon response are present on a chromosome of the genetically engineered bacterium. In further embodiments, one or both of: i) expressible nucleic acid sequences encoding the one or more gene products of interest, and ii) expressible nucleic acid sequences encoding the one or more factors that inhibit a mammalian interferon response, are present on a plasmid. In addition, the one or more factors that inhibit a mammalian interferon response may be of viral origin. In some embodiments, the one or more gene products of interest may be tuberculosis antigens. In further embodiments, the genetically engineered bacterium is a *shigella* bacterium or a *mycobacterium*.

The invention further provides a method for inducing an immune response to an antigen of interest in a mammal. The method comprises the step of administering to the mammal a genetically engineered bacterium, comprising nucleic acid sequences encoding the antigen of interest; and nucleic acid sequences encoding one or more factors that inhibit a mammalian interferon response. The nucleic acid sequences encoding the one or more passenger genes are operably linked to a eukaryotic promoter, and the nucleic acid sequences encoding the one or more factors that inhibit a mammalian type I interferon response are operably linked to a eukaryotic promoter or a prokaryotic promoter. In one embodiment of the invention, the antigen of interest is a *Mycobacterium tuberculosis* antigen. In some embodiments, transcription of the expressible nucleic acid sequences is controlled by eukaryotic promoters. In other embodiments, transcription of the expressible nucleic acid sequences encoding the one or more factors that inhibit a mammalian interferon response is controlled by prokaryotic promoters. In yet other embodiments, the expressible nucleic acid sequences encoding the one or more factors that inhibit a mammalian interferon response are present on a chromosome of the genetically engineered bacterium. In some embodiments, one or both of: i) expressible nucleic acid sequences encoding the antigen of interest, and ii) expressible nucleic acid sequences encoding the one or more factors that inhibit a mammalian interferon response, are present on a plasmid. In further embodiments, the one or more factors that inhibit a mammalian interferon response are of viral origin.

DETAILED DESCRIPTION OF THE PREFERRED EMBODIMENTS OF THE INVENTION

Figure 1:
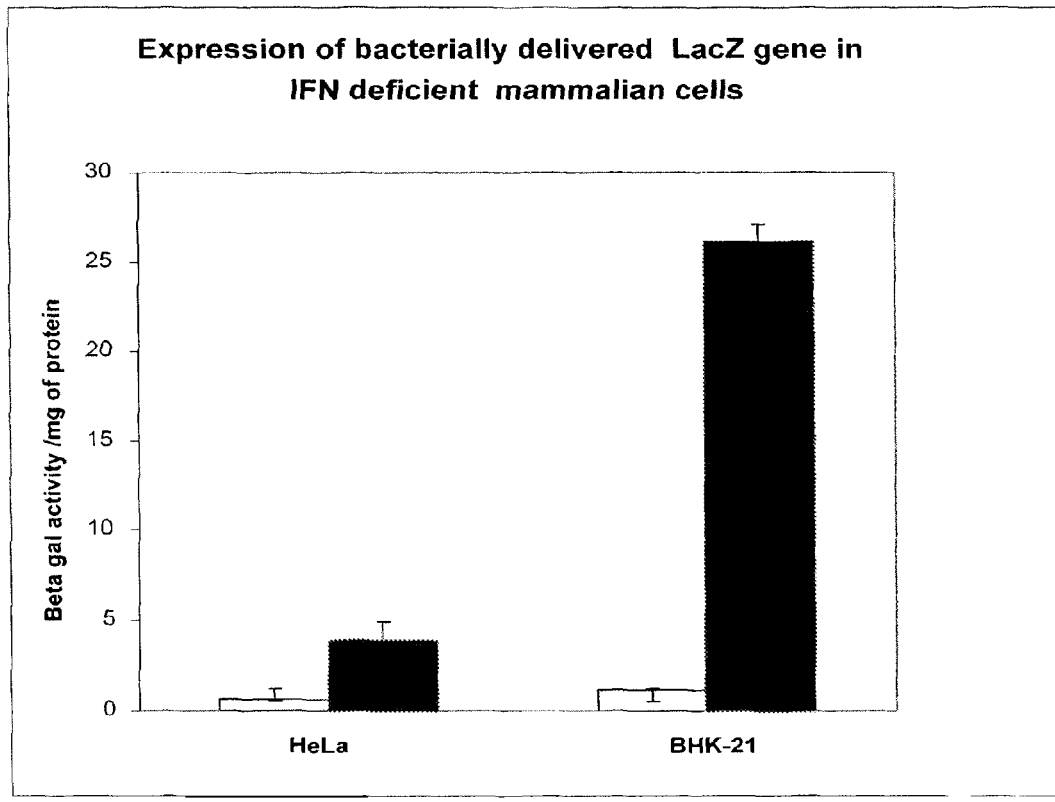
FIG. 1. Beta-galactosidase activity of cell lysates after invasion of HeLa or BHK-21 cells (IFN deficient) with *Shigella flexneri* NCD1 carrying a plasmid encoding eukaryotic expression of β-galactosidase. Black bar indicates β-galactosidase activity from cells post invasion with a bacterial strain harboring a plasmid encoding the lacZ gene; white bar indicates β-galactosidase activity from cells post invasion with a bacterial strain minus the lacZ plasmid.

The recombinant bacterial expression vectors of the present invention are genetically engineered to encode factors that eliminate, attenuate or suppress the type I interferon response that is usually mounted by mammalian host cells in response to invasion by a bacterium. These factors may be expressed by the bacterial vector cell or may be encoded in nucleic acids which are translated in the eukaryotic host cell. Attenuation or elimination of the IFN response in the eukaryotic host cell permits efficient transcription and translation of proteins and peptides of interest from vector introduced nucleic acids. Such vectored molecules may encode peptides and proteins that are necessary for the bacteria's reproduction and survival, as well as "passenger" molecules of interest contained within the bacterium. Examples of passenger nucleic acids of interest include but are not limited to, for example, antigens that the bacterium has been genetically engineered to encode. Because the eukaryotic host cell's type I IFN response is attenuated, the antigens are expressed persistently and at a level sufficient to cause the host cell to mount an immune response to the antigens. The bacterial expression vectors of the invention are thus ideal for use in vaccine preparations.

The bacterial expression vectors of the invention are genetically engineered to encode factors that eliminate, attenuate or suppress the type I IFN response. Those of skill in the art will recognize that many viruses encode factors that target specific mediators of IFN responses. These factors can be referred to as IFN response antagonists. Among the best characterized viral targets are protein kinase R (PKR), RNaseL activating (2'-5') oligoadenylate synthetase and the Interferon Regulatory Factor (IRF) family of proteins.

Such mechanisms are encoded by a variety of viruses, examples of which include but are not limited to: rotavirus non structural protein1 (NSP1); influenza-A virus non structural protein 1 (NS1); adenovirus associated RNA I and II (VAI and II); vaccinia virus E3L; hepatitis C virus non structural protein 5A (NS5A); simian virus-V protein; Sendai virus C protein; etc.

While in some embodiments, the factors that inhibit the IFN response are derived from viruses, such factors may be obtained from other sources, for example, from the host cell (e.g. suppressors of cytokine signaling, SOCS), dominant negative alleles of PKR and dominant negative alleles of RNaseL) and may be utilized in the practice of the present invention. Any factor that suppresses or attenuates the type I IFN response and which is encoded by a nucleic acid sequence that can be genetically engineered into and successfully expressed from a bacterial expression vector or delivered to eukaryotic cells by a bacterial vector may be used in the practice of the present invention.

By "bacterial expression vector" we mean a bacterial cell that has been genetically engineered to contain and express or deliver nucleic acid sequences of interest. Examples of bacteria which can be utilized in this manner include but are not limited to *Campylobacter* spp, *Neisseria* spp., *Haemophilus* spp, *Aeromonas* spp, *Francisella* spp, *Yersinia* spp, *Klebsiella* spp, *Bordetella* spp, *Legionella* spp, *Corynebacterium* spp, *Citrobacter* spp, *Chlamydia* spp, *Brucella* spp, *Pseudomonas* spp, *Helicobacter* spp, or *Vibrio* spp.

The particular *Campylobacter* strain employed is not critical to the present invention. Examples of *Campylobacter* strains that can be employed in the present invention include but are not limited to: *C. jejuni* (ATCC Nos. 43436, 43437, 43438), *C. hyointestinalis* (ATCC No. 35217), *C. fetus* (ATCC No. 19438) *C. fetalis* (ATCC No. 33709) *C. doylei* (ATCC No. 49349) and *C. coli* (ATCC Nos. 33559, 43133).

The particular *Yersinia* strain employed is not critical to the present invention. Examples of *Yersinia* strains which can be employed in the present invention include: *Y. enterocolitica* (ATCC No. 9610) or *Y. pestis* (ATCC No. 19428), *Y. enterocolitica* Ye03-R2 (al Hendy et al., Infect. Immun., 60:870; 1992) or *Y. enterocolitica* aroA (O'Gaora et al., Micro. Path., 9:105; 1990).

The particular *Klebsiella* strain employed is not critical to the present invention. Examples of *Klebsiella* strains that can be employed in the present invention include *K. pneumoniae* (ATCC No. 13884).

The particular *Bordetella* strain employed is not critical to the present invention. Examples of *Bordetella* strains which can be employed in the present invention include *B. pertussis*, and *B. bronchiseptica* (ATCC No. 19395).

The particular *Neisseria* strain employed is not critical to the present invention. Examples of *Neisseria* strains that can be employed in the present invention include *N. meningitidis* (ATCC No. 13077) and *N. gonorrhoeae* (ATCC No. 19424), *N. gonorrhoeae* MS11 aro mutant (Chamberlain et al., Micro. Path., 15:51-63; 1993).

The particular *Aeromonas* strain employed is not critical to the present invention. Examples of *Aeromonas* strains that can be employed in the present invention include *A. salminocida* (ATCC No. 33658), *A. schuberii* (ATCC No. 43700), *A. hydrophila*, *A. eucrenophila* (ATCC No. 23309).

The particular *Francisella* strain employed is not critical to the present invention. Examples of *Francisella* strains that can be employed in the present invention include *F. tularensis* (ATCC No. 15482).

The particular *Corynebacterium* strain employed is not critical to the present invention. Examples of *Corynebacterium* strains that can be employed in the present invention include *C. pseudotuberculosis* (ATCC No. 19410).

The particular *Citrobacter* strain employed is not critical to the present invention. Examples of *Citrobacter* strains that can be employed in the present invention include *C. freundii* (ATCC No. 8090).

The particular *Chlamydia* strain employed is not critical to the present invention. Examples of *Chlamydia* strains that can be employed in the present invention include *C. pneumoniae* (ATCC No. VR1310).

The particular *Haemophilus* strain employed is not critical to the present invention. Examples of *Haemophilus* strains that can be employed in the present invention include *H. influenzae* (Lee et al., J. Biol. Chem. 270:27151; 1995), *H. somnus* (ATCC No. 43625).

The particular *Brucella* strain employed is not critical to the present invention. Examples of *Brucella* strains that can be employed in the present invention include *B. abortus* (ATCC No. 23448).

The particular *Legionella* strain employed is not critical to the present invention. Examples of *Legionella* strains that can be employed in the present invention include *L. pneumophila* (ATCC No. 33156), or a *L. pneumophila* mip mutant (Ott, FEMS Micro. Rev., 14:161; 1994).

The particular *Pseudomonas* strain employed is not critical to the present invention. Examples of *Pseudomonas* strains that can be employed in the present invention include *P. aeruginosa* (ATCC No. 23267).

The particular *Helicobacter* strain employed is not critical to the present invention. Examples of *Helicobacter* strains that can be employed in the present invention include *H. pylori* (ATCC No. 43504), *H. mustelae* (ATCC No. 43772).

The particular *Vibrio* strain employed is not critical to the present invention. Examples of *Vibrio* strains that can be employed in the present invention include *Vibrio cholerae* (ATCC No. 14035), *Vibrio cincinnatiensis* (ATCC No. 35912), *V. cholerae* RSI virulence mutant (Taylor et al., J. Infect. Dis., 170:1518-1523; 1994) and *V. cholerae* ctxA, ace, zot, cep mutant (Waldor J et al., Infect. Dis., 170:278-283; 1994).

In a preferred embodiment, the bacterial strain from which the vector strain is developed in the present invention includes bacteria that possess the potential to serve both as a carrier and as a vaccine vectors, such as the Enterobacteriaceae, including but not limited to *Escherichia* spp, *Shigella* spp, and *Salmonella* spp. Gram-positive and acid-fast vector strains could similarly be constructed from *Listeria monocytogenes* or *Mycobacterium* spp.

The particular *Escherichia* strain employed is not critical to the present invention. Examples of *Escherichia* strains which can be employed in the present invention include *Escherichia coli* strains DH5α, HB 101, HS-4, 4608-58, 1184-68, 53638-C-17, 13-80, and 6-81 (See, e.g. Sambrook et al., supra; Grant et al., supra; Sansonetti et al., Ann. Microbiol. (Inst. Pasteur), 132A:351; 1982), enterotoxigenic *E. coli* (See, e.g. Evans et al., Infect. Immun., 12:656; 1975), enteropathogenic *E. coli* (See, e.g. Donnenberg et al., J. Infect. Dis., 169:831; 1994), enteroinvasive *E. coli* (See, e.g. Small et al., Infect Immun., 55:1674; 1987) and enterohemorrhagic *E. coli* (See, e.g. McKee and O'Brien, Infect. Immun., 63:2070; 1995).

The particular *Salmonella* strain employed is not critical to the present invention. Examples of *Salmonella* strains that can be employed in the present invention include *S. typhi* (see, e.g. ATCC No. 7251), *S. typhimurium* (see, e.g. ATCC No. 13311), *Salmonella galinarum* (ATCC No. 9184), *Salmonella enteriditis* (see, e.g. ATCC No. 4931) and *Salmonella typhimurium* (see, e.g. ATCC No. 6994). *S. typhi* aroC, aroD double mutant (see, e.g. Hone et al., Vacc., 9:810-816; 1991), *S. typhimurium* aroA mutant (see, e.g. Mastroeni et al., Micro. Pathol., 13:477-491; 1992).

The particular *Shigella* strain employed is not critical to the present invention. Examples of *Shigella* strains that can be employed in the present invention include *Shigella flexneri* (see, e.g. ATCC No. 29903), *Shigella flexneri* CVD1203 (see, e.g. Noriega et al., Infect. Immun. 62:5168; 1994), *Shigella flexneri* 15D (see, e.g. Sizemore et al., Science 270:299; 1995), *Shigella sonnei* (see, e.g. ATCC No. 29930), and *Shigella dysenteriae* (see, e.g. ATCC No. 13313).

The particular *Mycobacterium* strain employed is not critical to the present invention. Examples of *Mycobacterium* strains that can be employed in the present invention include *M. tuberculosis* CDC1551 strain (See, e.g. Griffith et al., Am. J. Respir. Crit. Care Med. August; 152(2):808; 1995), *M. tuberculosis* Beijing strain (Soolingen et al., 1995) H37Rv strain (ATCC#:25618), *M. tuberculosis* pantothenate auxotroph strain (Sambandamurthy, Nat. Med. 2002 8(10):1171; 2002), *M. tuberculosis* rpoV mutant strain (Collins et al., Proc Natl Acad Sci USA. 92(17):8036; 1995), *M. tuberculosis* leucine auxotroph strain (Hondalus et al., Infect. Immun. 68(5):2888; 2000), Bacille Calmette-Guérin (BCG) Danish strain (ATCC #35733), BCG Japanese strain (ATCC #35737), BCG, Chicago strain (ATCC #27289), BCG Copenhagen strain (ATCC #: 27290), BCG Pasteur strain (ATCC #: 35734), BCG Glaxo strain (ATCC #: 35741), BCG Connaught strain (ATCC #35745), BCG Montreal (ATCC #35746).

The particular *Listeria monocytogenes* strain employed is not critical to the present invention. Examples of *Listeria monocytogenes* strains which can be employed in the present invention include *L. monocytogenes* strain 10403S (e.g. Stevens et al., J. Virol 78:8210-8218; 2004) or mutant *L. monocytogenes* strains such as (i) actA plcB double mutant (Peters et al., FEMS Immunology and Medical Microbiology 35: 243-253; 2003); (Angelakopoulous et al., Infect and Immunity 70: 3592-3601; 2002); (ii) dal dat double mutant for alanine racemase gene and D-amino acid aminotransferase gene (Thompson et al., Infect and Immunity 66:3552-3561; 1998).

In some embodiments of the invention, the bacteria are, in particular, *Shigella* species, in particular attenuated invasive *Shigella flexneri* 2a. These strains, MPC51 and NCD1 are derivatives of *S. flexneri* strain 2457T into which asd and murI deletion mutations have been introduced. The asd defect is complemented by the expression vector encoded asd allele and the murI mutation results in the inability of the strain to synthesize D-glutamate; hence, these strains are incapable of synthesizing a proper cell wall in the absence of diaminopimelic acid and D-glutamate, which promotes lysis of the bacterial cell after invasion of a eukaryotic cell. As measured by a gentamicin protection assay, the HeLa cell invasive behavior of the Δasd, ΔmurI double mutant MPC51 was similar to that of the parental strain and MPC51pYA3342 (plasmid encoding asd). The strain has been further modified by removal of the kanamycin resistance gene previously inserted in the chromosomal asd locus. The resultant strain, *Shigella flexneri* NCD1, is thus free of antibiotic resistance markers, still retains chromosomal deletions of the asd and murI genes, and is acceptable for pharmacologic use in humans under current regulatory requirements. NCD1 has also been shown to be invasive in HeLa and Caco-2 cells in a manner similar to the parent strain.

Generally, the bacterial expression vectors of the invention are genetically engineered to encode and deliver both the IFN inhibiting factors and one or more other genes of interest i.e. passenger genes. The passenger genes are typically heterologous transgenes that originate from another organism, such as another bacteria or pathogen, and may be from any organism. However, the "passenger gene" may also be a gene that naturally occurs in the bacterial vector itself (i.e. is derived from or originates from the bacteria that serves as a vector), but one or more additional copies are genetically engineered in the bacterial vector to be under the control of a promoter that, for example, increases the level of transcription above that which is typical for the bacteria, or a promoter that is specific for a particular type of host cell or tissue (e.g. lung, lymph node, dendritic cell, etc). Further, "passenger gene" is intended to refer not only to entire "genes" but to any sequence that encodes a peptide, polypeptide, protein, or nucleic acid of interest, i.e. an entire "gene" per se may not be included, but rather the portion of a gene that encodes a polypeptide or peptide of interest e.g. an antigenic peptide. Further, various other constructions may be encoded by passenger genes, e.g. chimeric proteins, or various mutant (either naturally occurring or genetically engineered) forms of an amino acid sequence. In addition, totally artificial amino acid sequences that do not appear in nature may also be encoded. The bacterial expression vector is genetically engineered to contain one or more of such "passenger genes", and may also encode multiple copies of individual passenger genes. The recombinant bacterial expression vector functions as a vector to carry the passenger gene(s) into host cells that are invaded by the bacterium, where the gene product is expressed, i.e. the gene sequences are expressible and transcription and/or translation of the gene product occurs within the host cell that is invaded by the bacterium. The sequences encoding the passenger genes are operatively (operably) linked to expression control sequences, particularly expression control sequences that allow expression within the eukaryotic host cell.

In particular, such passenger genes may encode one or more peptides or proteins that are antigens, and to which it is desired to elicit an immune response. Those of skill in the art will recognize that a wide variety of such antigens exists, including but not limited to those associated with infectious agents such as various viruses, bacteria, and fungi, etc. The viral pathogens, from which the viral antigens are derived, include, but are not limited to, Orthomyxoviruses, such as influenza virus (Taxonomy ID: 59771; Retroviruses, such as RSV, HTLV-1 (Taxonomy ID: 39015), and HTLV-II (Taxonomy ID: 11909), Papillomaviridae such as HPV (Taxonomy ID: 337043), Herpesviruses such as EBV Taxonomy ID: 10295); CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia (Taxonomy ID: 10245); Rotavirus (Taxonomy ID: 10912); and Parvoviruses, such as adeno-associated virus 1 (Taxonomy ID: 85106).

Examples of viral antigens can be found in the group including but not limited to the human immunodeficiency virus antigens Nef (National Institute of Allergy and Infectious Disease HIV Repository Cat. #183; Genbank accession #AF238278), Gag, Env (National Institute of Allergy and Infectious Disease HIV Repository Cat. #2433; Genbank accession #U39362), Tat (National Institute of Allergy and Infectious Disease HIV Repository Cat. #827; Genbank accession #M13137), mutant derivatives of Tat, such as Tat-31-45 (Agwale et al., Proc. Natl. Acad. Sci. USA 99:10037; 2002), Rev (National Institute of Allergy and Infectious Disease HIV Repository Cat. #2088; Genbank accession #L14572), and Pol (National Institute of Allergy and Infectious Disease HIV Repository Cat. #238; Genbank accession #AJ237568) and T and B cell epitopes of gp120 (Hanke and McMichael, AIDS Immunol Lett., 66:177; 1999); (Hanke, et al., Vaccine, 17:589; 1999); (Palker et al., J. Immunol., 142: 3612 3619; 1989) chimeric derivatives of HIV-1 Env and gp120, such as but not restricted to fusion between gp120 and CD4 (Fouts et al., J. Virol. 2000, 74:11427-11436; 2000); truncated or modified derivatives of HIV-1 env, such as but not restricted to gp140 (Stamatos et al., J Virol, 72:9656-9667; 1998) or derivatives of HIV-1 Env and/or gp140 thereof (Binley, et al., J Virol, 76:2606-2616; 2002); (Sanders, et al., J Virol, 74:5091-5100 (2000); (Binley, et al. J Virol, 74:627-643; 2000), the hepatitis B surface antigen (Genbank accession #AF043578); (Wu et al., Proc. Natl. Acad. Sci., USA, 86:4726 4730; 1989); rotavirus antigens, such as VP4 (Genbank accession #AJ293721); (Mackow et al., Proc. Natl. Acad. Sci., USA, 87:518 522; 1990) and VP7 (GenBank accession #AY003871); (Green et al., J. Virol., 62:1819 1823; 1988), influenza virus antigens such as hemagglutinin or (GenBank accession #AJ404627); (Pertmer and Robinson, Virology, 257:406; 1999); nucleoprotein (GenBank accession #AJ289872); (Lin et al., Proc. Natl. Acad. Sci., 97: 9654-9658; 2000) herpes simplex virus antigens such as thymidine kinase (Genbank accession #AB047378; (Whitley et al., In: New Generation Vaccines, pages 825-854).

The bacterial pathogens, from which the bacterial antigens are derived, include but are not limited to: *Mycobacterium* spp., *Helicobacter pylori, Salmonella* spp., *Shigella* spp., *E. coli, Rickettsia* spp., *Listeria* spp., *Legionella pneumoniae, Pseudomonas* spp., *Vibrio* spp., *Bacillus anthracis* and *Borellia burgdorferi*.

Examples of protective antigens of bacterial pathogens include the somatic antigens of enterotoxigenic *E. coli*, such as the CFA/I fimbrial antigen (Yamamoto et al., Infect. Immun., 50:925 928; 1985) and the nontoxic B subunit of the heat labile toxin (et al., Infect. Immun., 40:888-893; 1983); pertactin of *Bordetella pertussis* (Roberts et al., Vacc., 10:43-48; 1992), adenylate cyclase hemolysin of *B. pertussis* (Guiso et al., Micro. Path., 11:423-431; 1991), fragment C of tetanus toxin of *Clostridium tetani* (Fairweather et al., Infect. Immun., 58:1323 1326; 1990), OspA of *Borellia burgdorferi* (Sikand et al., Pediatrics, 108:123-128; 2001); (Wallich et al., Infect Immun, 69:2130-2136; 2001), protective paracrystalline-surface-layer proteins of *Rickettsia prowazekii* and *Rickettsia typhi* (Carl et al., Proc Natl Acad Sci USA, 87:8237-8241; 1990), the listeriolysin (also known as "Llo" and "Hly") and/or the superoxide dismutase (also know as "SOD" and "p60") of *Listeria monocytogenes* (Hess, J., et al., Infect. Immun. 65:1286-92; 1997); Hess, J., et al., Proc. Natl. Acad. Sci. 93:1458-1463; 1996); (Bouwer et al., J. Exp. Med. 175: 1467-71; 1992), the urease of *Helicobacter pylori* (Gomez-Duarte et al., Vaccine 16, 460-71; 1998); (Corthesy-Theulaz, et al., Infection & Immunity 66, 581-6; 1998), and the *Bacillus anthracis* protective antigen and lethal factor receptor-binding domain (Price, et al., Infect. Immun. 69, 4509-4515; 2001).

The parasitic pathogens, from which the parasitic antigens are derived, include but are not limited to: *Plasmodium* spp., such as *Plasmodium falciparum* (ATCC#: 30145); *Trypanosome* spp., such as *Trypanosoma cruzi* (ATCC#: 50797); *Giardia* spp., such as *Giardia intestinalis* (ATCC#: 30888D); *Boophilus* spp., *Babesia* spp., such as *Babesia microti* (ATCC#: 30221); *Entamoeba* spp., such as *Entamoeba histolytica* (ATCC#: 30015); *Eimeria* spp., such as *Eimeria maxima* (ATCC#40357); *Leishmania* spp. (Taxonomy ID: 38568); *Schistosome* spp., *Brugia* spp., *Fascida* spp., *Dirofilaria* spp., *Wuchereria* spp., and *Onchocerea* spp.

Examples of protective antigens of parasitic pathogens include the circumsporozoite antigens of *Plasmodium* spp. (Sadoff et al., Science, 240:336 337; 1988), such as the circumsporozoite antigen of *P. berghei* or the circumsporozoite antigen of *P. falciparum*; the merozoite surface antigen of *Plasmodium* spp. (Spetzler et al., Int. J. Pept. Prot. Res., 43:351-358; 1994); the galactose specific lectin of *Entamoeba histolytica* (Mann et al., Proc. Natl. Acad. Sci., USA, 88:3248-3252; 1991), gp63 of *Leishmania* spp. (Russell et al., J. Immunol., 140:1274 1278; 1988); (Xu and Liew, Immunol., 84: 173-176; 1995), gp46 of *Leishmania major* (Handman et al., Vaccine, 18:3011-3017; 2000) paramyosin of *Brugia malayi* (Li et al., Mol. Biochem. Parasitol., 49:315-323; 1991), the triose-phosphate isomerase of *Schistosoma mansoni* (Shoemaker et al., Proc. Natl. Acad. Sci., USA, 89:1842 1846; 1992); the secreted globin-like protein of *Trichostrongylus colubriformis* (Frenkel et al., Mol. Biochem. Parasitol., 50:27-36; 1992); the glutathione-S-transferase's of *Frasciola hepatica* (Hillyer et al., Exp. Parasitol., 75:176-186; 1992), *Schistosoma bovis* and *S. japonicum* (Bashir et al., Trop. Geog. Med., 46:255-258; 1994); and KLH of *Schistosoma bovis* and *S. japonicum* (Bashir et al., supra, 1994).

Alternatively, it may be desired to elicit an immune response to antigens that are not associated with infectious agents, for example, antigens associated with cancer cells, Alzheimer's disease, Type 1 diabetes, heart disease, Crohn's disease, multiple sclerosis, etc.

In addition, the passenger genes that are carried by the bacterium need not encode antigens, but may encode any peptide or protein of interest. For example, the methods of the invention can be used for the delivery of passenger molecules for correction of hereditary disorders. Such genes would include, for example, replacement of defective genes such as the cystic fibrosis transmembrane conductance regulator (CFTR) gene for cystic fibrosis; or the introduction of new genes such as the integrase antisense gene for the treatment of HIV; or genes to enhance Type I T cell responses such as interleukin-27 (IL-27); or genes to modulate the expression of certain receptors, metabolites or hormones such as cholesterol and cholesterol receptors or insulin and insulin receptors; or genes encoding products that can kill cancer cells such as tumor necrosis factor (TNF)-related apoptosis-inducing ligand (TRAIL); or a naturally occurring protein osteoprotegerin (OPG) that inhibits bone resorption; or to efficiently express complete-length humanized antibodies, for example, humanized monoclonal antibody that acts on the HER2/neu (erbB2) receptor on cancer cells.

In addition, the passenger genes may encode inhibitory RNAs such as "small inhibitory" siRNAs. As is known in the art, such RNAs are complementary to an mRNA of interest and bind to and prevent translation of the mRNA, e.g. as a means of preventing the expression of a gene product.

Similar methods can be used for delivery of passenger molecules to down regulate the immune system in order to prevent or control autoimmune diseases or other diseases of immune system. Examples include the prevention or treatment of diabetes mellitus, multiple sclerosis, lupus erythematosis and Crohn's disease and inflammatory joint and skin diseases. Other examples include fine tuning of immune responses that hamper specific immune responses such as down regulation of immune responses that divert the therapeutic immune responses to cancer and other diseases. For example, down regulation of Th2 responses when Th1 responses are appropriate for prevention and treatment of cancer, Leishmaniasis, tuberculosis, and HIV. This can be achieved by means of the present technology through manipulation of the immunosuppressive nature of the immune system in combination with the ability to express the suitable cytokine milieu for stimulation of the proper immune response and inhibition of improper immune responses.

In a preferred embodiment, the present invention relates to a method for the introduction of IFN resistance genes into host cells. Such a method would comprise introduction of the desired IFN resistance genes, along with sequences encoding a gene or nucleic acid sequence of interest, into a bacterial based delivery system such that the IFN resistance proteins and nucleic acid sequences of interest are expressed upon administering the bacteria to a host. The IFN inhibitor can be produced by the bacteria (e.g. *shigella*) or by the host cell. In other words, the IFN resistance genes can be expressed from a prokaryotic promoter or from a eukaryotic promoter. The gene or nucleic acid sequences of interest (passenger genes) are expressed by the host. Further, all genetic sequences may be either constitutively expressed or induced.

In yet another preferred embodiment, the present invention provides a method for the introduction of type I IFN resistance genes along with one or more genes of interest into cells in vitro. Such a method would comprise introduction of the genes encoding one or more proteins of interest along with one or more IFN resistance genes into, for example, attenuated or attenuated/inactivated *shigella* such that the desired proteins/peptides are produced upon administering the *shigella* to cells. *Shigella* infects several different cell types, such as BHK (baby hamster kidney cells), HeLa (human cervical epitheloid carcinoma), CaCo-2 (human colonic adenocarcinoma) and therefore is capable of delivering the desired passenger molecules into cells. Gene expression in the *shigella*-infected cells is enhanced by the inhibitor of the type I IFN response. Following nucleic acid delivery, the cells can be transplanted for therapeutic purposes, for gene therapy or used as reagents in diagnostic assays.

In these cases, the bacteria serve as "gene therapy" agents by delivering to the cell nucleic acid sequences that encode a desired substance and mediating its production in the cell. For example, delivering CXCR4/or CCR5 binding chemokine-encoding genes into the gut using *shigella* vectors could be considered for treatment for HIV-1 infection. Procedures for genetically engineering bacteria are well-known to those of skill in the art, and guidance for carrying out such procedures are well known. Methods to attenuate *E. coli, Salmonella, Mycobacteria, Shigella*, and *Listeria* are well known to those skilled in the art (Evans et al., J. of Immuno., vol. 120, 1978, p. 1423); (Noriega et al., Infect. Immun., 62(11):5168-5172 1994); (Hone et al., Vacc., 9:810-816; 1991).

For example, a method for the delivery of a desired gene or genes into a cell may include introducing the gene of interest into a strain of bacteria. In accordance with the present invention, an anti-IFN response gene or genes can be introduced into the bacterial chromosome or virulence plasmid by methods well known to those of skill in the art or alternatively can be carried in a replicating or nonreplicating plasmid. The vectors of interest can be introduced into the bacterium, for example, via transformation, electroporation, transfection, conjugation, etc. The recombinant DNA procedures used in the construction of the strains and bacterial vectors include but are not limited to: polymerase chain reaction (PCR), restriction endonuclease (herein referred to as "RE") digestions, DNA ligation, agarose gel electrophoresis, DNA purification, and dideoxynucleotide sequencing, which are described elsewhere (Miller, *A Short Course in Bacterial Genetics*, Cold Spring Harbor Laboratory Press, Cold Spring Harbor, N.Y.; 1992); (Bothwell et al., Methods for Cloning and Analysis of Eukaryotic Genes, Eds., Jones and Bartlett Publishers Inc., Boston, Mass. 1990); and (Ausubel et al., Current Protocols in Molecular Biology, vol. 2:10.8.1-10.8.13, 1992), bacteriophage-mediated transduction (de Boer et al., Cell, 56:641-649; 1989); (Miller, supra, 1992) and (Ausubel et al., supra), or chemical (Bothwell et al., supra); (Ausubel et al., supra); (Feigner et al., supra); and (Farhood, supra), electroporation (Bothwell et al., supra); (Ausubel et al., supra); (Sambrook, *Molecular Cloning: A Laboratory Manual*, Cold Spring Harbor Laboratory Press, Cold Spring Harbor, N.Y.; 1992) and physical transformation techniques (Bothwell et al., supra). The genes can be incorporated in phage (de Boer et al., supra), plasmids vectors (Curtiss, In: New Generation Vaccines: The Molecular Approach, Ed., Marcel Dekker, Inc., New York, N.Y., pages 161-188 and 269-288 1989) or spliced into the chromosome (Hone et al., supra) of the target strain.

Gene sequences can be made synthetically using, for example, an Applied Biosystems ABI™ 3900 High-Throughput DNA Synthesizer (Foster City, Calif. 94404 U.S.A.) using procedures provided by the manufacturer. To synthesize large sequences i.e. greater than about 200 bp, a series of segments of the full-length sequence are generated by PCR and ligated together to form the full-length sequence using procedures well know in the art. However, smaller sequences, i.e. those smaller than about 200 bp, can be made synthetically in a single round.

Recombinant plasmids may be introduced into bacterial strains by electroporation using, for example, a BioRad Gene-Pulser. Nucleotide sequencing to verify cDNA sequences may be accomplished by standard automated sequencing techniques (e.g. using an Applied Biosystems automated sequencer, model 373A). DNA primers for DNA sequencing and polymerase chain reaction (herein referred to as "PCR") may be produced synthetically.

In some embodiments of the invention, the bacteria that are genetically engineered are attenuated invasive *Shigella flexneri* and the genes that are introduced into the bacteria are the adenovirus VAI genes, NSP1 of rotavirus, and/or NS1 of influenzae virus which are cloned under the control of a eukaryotic promoter and are introduced into the bacterium by electroporation.

The present invention also provides preparations for administering the recombinant bacterial expression vectors of the invention. In particular, vaccine preparations for use in eliciting immune responses are provided. The preparations include at least one genetically engineered bacterial strain as described herein, and a pharmacologically suitable carrier. The preparation of such compositions (e.g. for use as vaccines) is well known to those of skill in the art. Typically, such compositions are prepared either as liquid solutions or suspensions, however, solid forms such as tablets, pills, powders and the like are also contemplated. Solid forms suitable for solution in, or suspension in, liquids prior to administration may also be prepared. The preparation may also be emulsified. The active ingredients may be mixed with excipients that are pharmaceutically acceptable and compatible with the active ingredients. Suitable excipients are, for example, water, saline, dextrose, raffinose, glycerol, ethanol and the like, or combinations thereof. In addition, the composition may contain minor amounts of auxiliary substances such as wetting or emulsifying agents, pH buffering agents, and the like. The vaccine preparations of the present invention may further comprise an adjuvant, suitable examples of which include but are not limited to Seppic, Quil A, Alhydrogel, etc.

If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of recombinant bacteria in the formulations may vary. However, in general, the amount in the formulations will be from about 1-99 percent. Further, the preparations of the present invention may contain a single type of recombinant bacteria or more than one type of recombinant bacteria.

In the case of vaccine preparations, the present invention also provides methods of eliciting an immune response to antigens encoded by the bacterium, and methods of vaccinating a mammal against diseases or conditions associated with such antigens. By eliciting an immune response, we mean that administration of the vaccine preparation of the present invention causes the synthesis of specific antibodies (at a titer in the range of 1 to $1\times10^6$, preferably $1\times10^3$, more preferable in the range of about $1\times10^3$ to about $1\times10^6$, and most preferably greater than $1\times10^6$) and/or cellular proliferation, as measured, e.g. by $^3$H thymidine incorporation. The methods involve administering a composition comprising a bacterial strain of the present invention in a pharmacologically acceptable carrier to a mammal. The vaccine preparations of the present invention may be administered by any of the many suitable means which are well known to those of skill in the art, including but not limited to by injection, orally, intranasally, by ingestion of a food product containing the recombinant bacteria, etc. In preferred embodiments, the mode of administration is oral, subcutaneous, intradermal or intramuscular.

The invention is further illustrated by the following non-limiting Examples.

EXAMPLES

Example 1

Induction of Type I Interferon Response in Host Cells by a Recombinant *Shigella* Vector The ability of bacteria to induce a type 1 interferon response in mammalian cells was tested and the nature of the response was analyzed. Experimental conditions were as follows: Semi-confluent monolayers of HeLa cells were exposed to *Shigella flexneri* carrying a RNA passenger molecule for 1 hour at a multiplicity of infection (MOI) of 100 in a 6 well plate at 37° C. Cells were washed twice with Dulbecco's Modified Eagles's Medium (DMEM). Medium containing 150 µg/ml gentamicin was added to the cells for 1 hour to kill extracellular bacteria. Subsequently, cells were washed twice, and DMEM with 10% fetal bovine serum (FBS) was added and the infected cells were allowed to incubate for 20 h. Cells were then washed twice with phosphate buffered saline (PBS) and total RNA was isolated using an RNeasy mini kit (Qiagen). The Human Interferons and Receptors RT²Profiler™ PCR Array (Superarray Biosciences) was utilized to identify up regulation or down regulation of the expression of 84 interferon related genes.

The results are presented in Table 1. As can be seen, invasion of the *shigella* vector into the human cells led to transcriptional induction of type I IFNs and IFN stimulated genes such 2'-5'-oligoadenylate synthetase (2'-5'-OAS). Of the 89 genes that were surveyed, 74 showed more than a 2-fold increase in transcription.

In addition, further experiments showed that expression of a reporter gene from a plasmid DNA passenger molecule delivered by *shigella* into IFN-α/β deficient cells was enhanced compared to the cells having an intact IFN system (FIG. 1).

These results clearly suggest that IFN stimulated genes suppress the expression of genes from passenger molecules delivered to mammalian cells by bacterial vectors.

TABLE 1

Differential IFN associated gene expression: comparison of *shigella*-invaded HeLA cells vs non-invaded HeLa cells.

| Gene | Fold Induction |
| --- | --- |
| ADAR (adenosine deaminase acting on RNA) | 3.37 |
| CNTFR (ciliary neurotrophic factor receptor) | 3.54 |
| CRLF2 (cytokine receptor-like factor 2) | 3.10 |
| CSF2RA (colony stimulating factor 2 receptor) | 2.80 |
| CSF3R (colony stimulating factor 3 receptor) | 5.44 |
| CXCL10 (chemokine (C-X-C motif) ligand 10) | 649.87 |
| EBI3 (Epstein-Barr virus induced gene 3) | 4.30 |
| F3 Coagulation factor III (thromboplastin, tissue factor) | 2.90 |
| IL20RB (interleukin 20 receptor beta) | 1.35 |
| ISG15 (interferon stimulated gene 15) | 13.87 |
| IFI6 (interferon, alpha-inducible protein 6) | 18.69 |
| IFI16 (interferon, gamma-inducible protein 16) | 5.11 |
| IFI27 (interferon, alpha-inducible protein 27) | 52.13 |
| IFI30 (interferon, gamma-inducible protein 30) | 1.56 |
| IFI35 (interferon-induced protein 35) | 4.54 |
| IFI44 (interferon-induced protein 44) | 5.22 |
| IFI44L (interferon-induced protein 44-like) | 7.33 |
| IFIH1 (interferon induced with helicase C domain 1) | 65.53 |
| IFIT1 (interferon-induced protein with tetratricopeptide repeats-1) | 12.94 |
| IFIT1L (interferon-induced protein with tetratricopeptide repeats-1-like) | 13.21 |
| IFIT2 (interferon-induced protein with tetratricopeptide repeats-2) | 6.47 |
| IFIT3 (interferon-induced protein with tetratricopeptide repeats-3) | 19.08 |
| IFITM1 (interferon induced transmembrane protein 1) | 3.47 |
| IFITM2 (interferon induced transmembrane protein 2) | 0.85 |
| IFNA1 (interferon, alpha 1) | 2.34 |
| IFNA14 (interferon, alpha 14) | 3.02 |
| IFNA2 (interferon, alpha 2) | 19.48 |
| IFNA21 (interferon, alpha 21) | 14.66 |
| IFNA4 (interferon, alpha 4) | 7.86 |
| IFNA5 (interferon, alpha 5) | 37.90 |
| IFNA6 (interferon, alpha 6) | 3.28 |
| IFNA8 (interferon, alpha 8) | 3.77 |
| IFNAR1 (interferon (alpha, beta and omega) receptor 1) | 2.44 |
| IFNAR2 (interferon (alpha, beta and omega) receptor 2) | 3.72 |
| IFNB1 (interferon, beta 1) | 21.92 |
| IFNE1 (interferon epsilon 1) | 1.72 |
| IFNG (interferon, gamma) | 6.21 |
| IFNGR1 (interferon-gamma receptor 1) | 8.08 |
| IFNGR2 (interferon-gamma receptor 2) | 3.13 |
| IFNK (interferon, kappa) | 5.40 |
| IFNW1 (interferon, omega 1) | 18.18 |
| IFRD1 (interferon-related developmental regulator 1) | 8.36 |
| IFRD2 (interferon-related developmental regulator 2) | 1.07 |
| IL10RA (interleukin 10 receptor, alpha) | 9.67 |
| IL10RB (interleukin 10 receptor, beta) | 3.28 |
| IL11RA (interleukin 11 receptor, alpha) | 2.02 |
| IL12B (interleukin 12, beta) | 31.00 |
| IL13RA1 (interleukin 13 receptor, alpha-1) | 1.64 |
| IL15 (interleukin 15) | 2.59 |
| IL20RA (interleukin 20 receptor, alpha) | 2.82 |
| IL21R (interleukin 21 receptor) | 6.21 |
| IL22RA2 (interleukin 22 receptor, alpha-2) | 8.78 |
| IL28A (interleukin 28, alpha) | 5.26 |
| IL28RA (interleukin 28 receptor, alpha) | 1.94 |
| IL29 (interleukin 29) | 25.71 |
| IL2RB (interleukin 2 receptor, beta) | 9.47 |
| IL2RG (interleukin 2 receptor, gamma) | 26.61 |
| IL31RA (interleukin 31 receptor, alpha) | 5.22 |
| IL3RA (interleukin 3 receptor, alpha) | 12.85 |
| IL4R (interleukin 4 receptor) | 4.33 |
| IL5RA (interleukin 5 receptor, alpha) | 3.24 |
| IL6 (interleukin 6) | 42.34 |
| IL6R (interleukin 6 receptor) | 11.91 |
| IL7R (interleukin 7 receptor) | 22.38 |
| IL9R (interleukin 9 receptor) | 1.91 |

TABLE 1-continued

Differential IFN associated gene expression: comparison of shigella-invaded HeLA cells vs non-invaded HeLa cells.

| Gene | Fold Induction |
|---|---|
| IRF1 (interferon regulatory factor 1) | 20.03 |
| IRF2 (interferon regulatory factor 2) | 3.85 |
| IRF2BP1 (interferon regulatory factor 2 binding protein 1) | 2.32 |
| IRF2BP2 (interferon regulatory factor 2 binding protein 2) | 4.94 |
| IRF3 (interferon regulatory factor 3) | 1.88 |
| IRF4 (interferon regulatory factor 4) | 49.32 |
| IRF5 (interferon regulatory factor 5) | 5.75 |
| IRF6 (interferon regulatory factor 6) | 5.67 |
| IRF7 (interferon regulatory factor 7) | 3.02 |
| IRF8 (interferon regulatory factor 8) | 30.36 |
| IRGM (immunity-related GTPase family, M) | 350.68 |
| LEPR (leptin receptor) | 2.23 |
| MPL (myeloproliferative leukemia protein) | 4.64 |
| MX1 (Myxovirus (influenza) resistance 1) | 13.40 |
| OAS1 (2'-5'-oligoadenylate synthetase) | 8.66 |
| PSME1 (proteasome (prosome, macropain) activator subunit 1) | 1.13 |
| PYHIN1 (pyrin and HIN domain) | 2.63 |
| SP110 (nuclear body protein) | 1.82 |
| TTN (encodes central sarcomeric protein, titin) | 45.07 |
| B2M (beta-2-microglobulin) | 2.21 |
| HPRT1 (hypoxanthine phosphoribosyltransferase 1) | 0.68 |
| RPL13A (ribosomal protein L13a) | 0.49 |
| GAPDH (glyceraldehyde-3-phosphate dehydrogenase) | 0.98 |
| ACTB (actin, beta) | 1.39 |

Example 2

Construction of Bacterial Delivery Systems that Counter the Negative Effects Of the Type I IFN Response on Expression of Passenger Nucleic Acids Delivered by Bacterial Vectors This example describes the construction and use of two bacterial delivery systems that reduced the negative effects of IFNs on expression of a passenger nucleic acids. In both cases, nucleic acids were genetically engineered into attenuated, invasive *Shigella flexneri* strains by electroporation. *Shigella flexneri* was selected because it is naturally invasive in many tissue culture cell lines and animal models. The *Shigella* strain carries introduced chromosomal mutations that cause it to lyse after invasion of eukaryotic cells and escape from the endocytic vesicle, enabling the release of passenger molecules into the eukaryotic cell cytoplasm.

Figure 2:
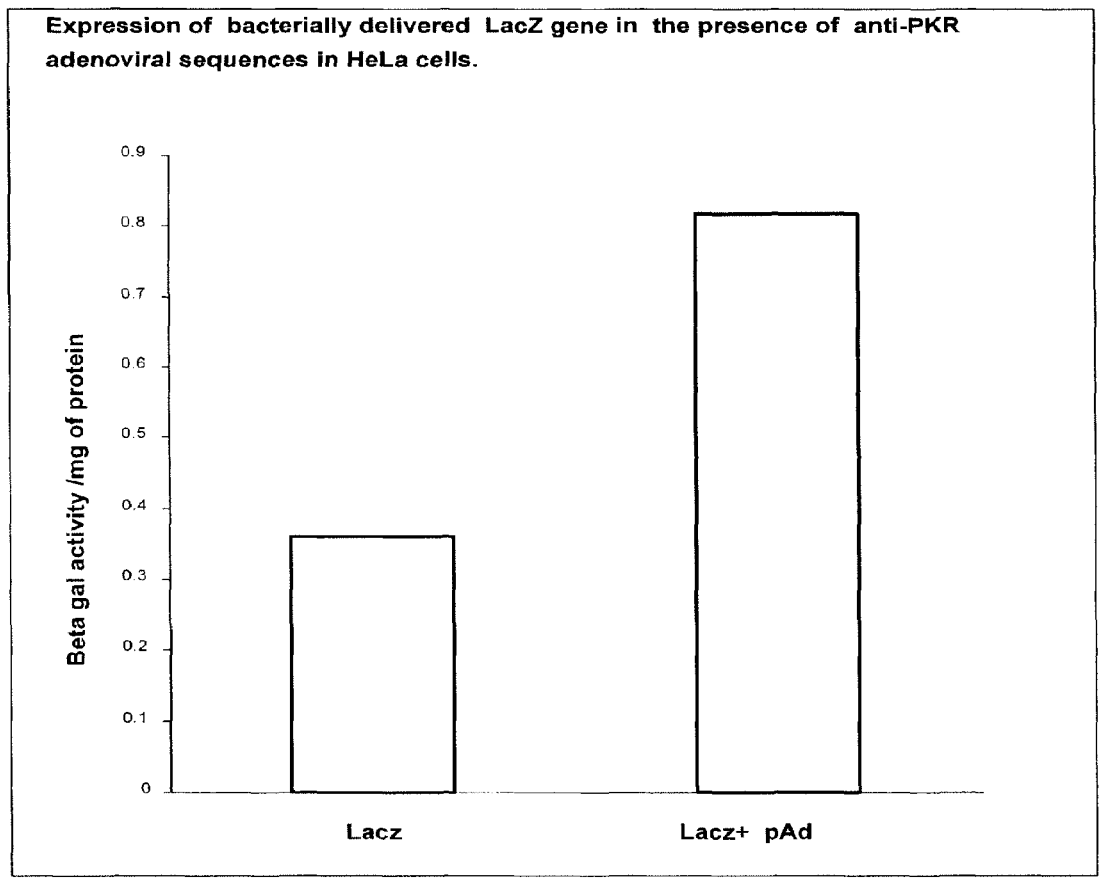
FIG. 2. β-galactosidase activity of lysates of HeLa cells after invasion with *Shigella flexneri* NCD1 harboring a plasmid encoding β-galactosidase and after co-invasion with *Shigella flexneri* NCD1 encoding an adenovirus derived inhibitor of PKR (adenovirus-associated I, VAI).

In the first set of experiments, electro-competent *Shigella flexneri* strain NCD1 was prepared and electroporated with the commercially available *E. coli* beta-galactosidase-expressing reporter vector pcDNA3.1/His/lacZ (Invitrogen). Reporter vector pcDNA3.1/His/lacZ expresses *E. coli* beta-galactosidase under the control of the human cytomegalovirus (CMV) promoter in mammalian cells, permitting the ready analysis of mammalian-mediated gene expression after delivery of the vector. The interferon resistance gene used in this experiment was the adenovirus-associated I (VAI) RNA gene. The adenovirus RNA gene is known to be transcribed by RNA polymerase III in large amounts after adenovirus infection (Reich et al., J. Mol. Biol. 17, 428, 1966; Price et al., J. Virol. 9, 62, 1972; Weinmann et al., Proc. Nat. Acad. Sci. USA 71, 3426; Soderlund et al., Cell 7, 585, 1976.) Adenoviruses use the virus-encoded virus-associated RNA as a defense against cellular antiviral responses by blocking the activation of the interferon-induced, double-stranded RNA-activated protein kinase PKR (Galabru J, Katze M G, Robert N, Hovanessian A G. Eur J. Biochem. 1989 Jan. 2; 178(3): 581-9). The pAdVAntage vector that contains the Adenovirus Virus-Associated I (VAI) RNA gene on a 1,724 bp insert was also electroporated into the *Shigella flexneri* NCD1 strain. Invasion of HeLa cells by electroporation with *Shigella flexneri* strains was carried out as described in Example 1. Briefly, to test the anti-interferon effect of the VAI gene, HeLa cells were co-invaded with *Shigella flexneri* NCD1 containing the beta-galactosidase reporter vector (pcDNA3.1/His/lacZ) and *Shigella flexneri* NCD1 containing the pAdVAntage vector, or with *Shigella flexneri* NCD1 strain alone (without a vector). After 24 hours, beta-galactosidase assay reagents (Stratagene) were used both for cell lysis and for the assay of beta-galactosidase activity in cell extracts. The results are presented in FIG. 2. As can be seen, a large increase in beta-galactosidase activity was observed in the HeLa cells invaded by *shigella* that contained both the beta-galactosidase reporter vector and the anti-interferon pAdVAntage vector.

Figure 3:
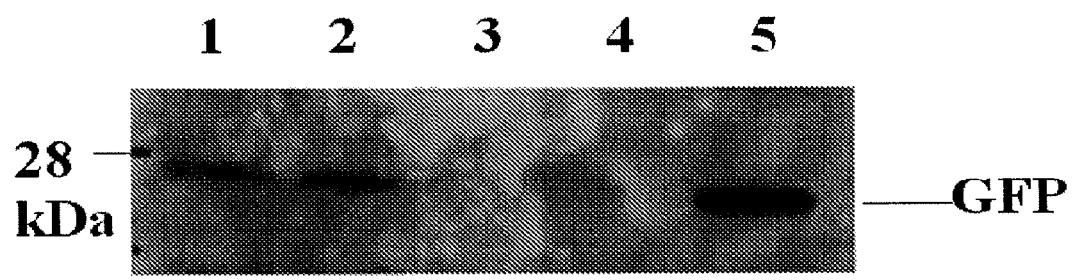
FIG. 3. Immunoblot showing transgene expression of green fluorescent protein (GFP) protein in HeLa cells post invasion with *Shigella flexneri* strain MPC51 which carries a eukaryotic GFP reporter gene only (lane 4) or GFP plus NS1(lane 5) or NSP1 (lane 2). Lane 1: positive control; Lane 3: non-invaded HeLa cells.

Similarly, in the second set of experiments, a *shigella* vector strain containing recombinant double-stranded RNA nucleocapsids (rdsRN) carrying the reporter gene Green Fluorescent Protein (GFP) were electroporated with sequences encoding influenza-A NS1 or rotavirus NSP1 which were cloned into the eukaryotic expression vector pcDNA 3.1 zeo(+) (Invitrogen). The resulting *Shigella* strain thus contained both the GFP gene in the RNA nucleocapsid (rdsRN) and NSP1 or NS1 in pcDNA. BHK-21 and HeLa cells were invaded with the GFP and NSP1 or NS1-expression plasmid harboring *Shigella* strain. After 16 hours, invaded HeLa cells were tested for green fluorescence and the HeLa cell lysate was analyzed for GFP protein by immunoblotting. The fluorescence results showed that expression of GFP protein was enhanced in the cells which were invaded with an NS1- or NSP1-expression plasmid harboring *Shigella* strain, compared to cells invaded by a *Shigella* strain with only a GFP gene (data not shown). Immunoblotting of total protein produced by the eukaryotic cells confirmed higher GFP expression in cells invaded with a NS1 or NSP1-expression plasmid harboring *Shigella* strain (FIG. 3).

These findings show that expression of a gene encoding an inhibitor of the type I interferon response enhances the co-expression of a transgene encoding a protein of interest (e.g. beta-galactosidase or GFP) enhances the expression of the protein of interest. The results described in this Example are the first evidence showing that enhanced expression of a protein of interest can be obtained by attenuating the IFN response using a bacterial based delivery system.

The same or similar results are obtained in vivo in mammalian cells or tissues invaded by a genetically engineered bacterium encoding an antigen such as a tuberculosis antigen, and a factor that attenuates the IFN response. Expression of the antigen is greater in such a bacterium than if the factor was not produced. As a result, the mammalian host would successfully mount an immune response to the antigen.

Example 3

Construction of an Expression Vector Expressing an Interferon Resistance Gene in Both Bacteria and Mammalian Cells and a Protein of Interest Only in Mammalian Cells A plasmid vector is constructed to express the immunodominant gag peptide of HIV-1. A 600 bp fragment is PCR-amplified from a synthetic gag gene. The sequence is amplified using Accuprime DNA polymerase (Invitrogen, Carlsbad, Calif.) and primers including HpaI and NotI RE sites. The size of the amplified sequence is verified by agarose gel electrophoresis, and is purified using a QIAquick PCR purification kit by following manufacturer's instructions (Qiagen, Cat. No. 28106, Valencia, Calif.). The 600 bp gag gene is cloned into the EcoRV and NotI sites (New England Biolabs, Beverly, Mass.) of the expression vector plasmid pcDNA3.1zeo(+) (Invitrogen, Carlsbad, Calif.). Recombinant plasmids harboring the appropriate inserts are identified and the novel plasmid is designated pGAG4X.

An interferon resistance gene (e.g. NS1 or NSP1) is cloned into the pGAG4X vector under the control of an appropriate eukaryotic promoter (e.g.SV40 promoter) or prokaryotic promoter (e.g. house keeping promoter of arg1), or both, generating a dual expression vector. (The particular eukaryotic and prokaryotic promoter sequences described herein are not critical to the construction of the vector and other suitable promoters will occur to those of skill in the art.) Thus, this expression vector expresses an interferon resistance gene in both bacteria and mammalian cells; however the protein of interest (e.g. Gag of HIV-1) is expressed only in mammalian cells. This approach improves transcript stability an subsequent translation of passenger RNA/DNA and other molecules for the expression of foreign proteins of interest or inhibitory RNAs in mammalian cells.

Example 4

Use of a Recombinant Bacterial Expression Vector that is Genetically Engineered to Suppress the IFN Response as a Vaccine The efficacy of any bacterial live-vector vaccine rests with its ability to present sufficient foreign antigen to the human immune system to initiate the desired protective immune response. However, passenger DNA/RNA molecules may become unstable in vivo due to the host defense system, namely the IFN response, resulting in the loss of foreign genes and a decrease in the intended immune response. This invention provides a solution for the synthesis of high levels of antigen within host cells by attenuating the IFN defense system.

Delivery and expression of genes encoding IFN resistance and an antigen of interest may be accomplished by the inoculation of targeted cells (tissue, organism, etc.) with a non-pathogenic or attenuated bacterial vaccine vector that carries nucleic acids encoding the transgene of interest and a suppressor of the type I IFN response. Biological responses of interest include, but are not limited to: protective or modulatory immune responses; therapeutic responses; and down-regulation of gene expression (e.g. siRNA) and up-regulation of gene expression (e.g. cytokine expression) of host proteins.

Once a non-pathogenic or attenuated bacterial vaccine vector strain has been selected, the strain is modified to serve as an interferon response suppressing strain. This is accomplished using the strategies described above that entail introducing one or more IFN resistance genes into the strain.

To generate strains that contain type I IFN resistance genes and antigens of interest, in vitro synthesized gene(s) are introduced into the strains by electroporation and transformants are isolated on solid media under conditions that only permit the growth of strains that harbor and express a positive selection allele in the recombinant plasmid (e.g. antibiotic resistance or complementation of auxotrophy). One method of enhancing the inheritance of expression plasmids by live vectors involves construction of a passenger nucleic acids designed to complement an introduced mutation in the bacterial chromosome. In a plasmid-based complementation system, plasmids replicating in the cytoplasm of the bacterium express a critical protein required by the bacterium to grow and replicate; loss of such plasmids removes the ability of the bacterium to express the critical protein and results in cell death. (The phenomenon of plasmid loss during bacterial replication, which results in the death of any plasmid-less bacterium, is also referred to as "post segregational killing.") Such a system has been successfully employed in *Salmonella typhimurium* and is based on expression of the asd gene encoding aspartate β-semialdehyde dehydrogenase (Asd) (Galen et al., Gene. 1990; 49:29-35). Asd is a critical enzyme involved in the synthesis of structural components essential for the formation of the cell wall in gram-negative bacteria. Therefore, loss of plasmids encoding such a critical enzyme would be lethal for any bacterium incapable of synthesizing Asd from the chromosome.

The amount of such recombinant bacteria to be administered varies depending on the species of the subject, as well as the disease or condition that is being treated. Generally, the dosage employed is about $10^3$ to $10^{11}$ viable organisms, preferably about $10^3$ to $10^9$ viable organisms. The bacterial vector harboring the DNA/RNA passenger molecule is generally administered along with a pharmaceutically acceptable carrier or diluent. The particular phaimaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 10) alone (Levine et al., J. Clin. Invest., 79:888-902; 1987); (Black et al., J. Infect. Dis., 155:1260-1265; 1987), or bicarbonate buffer (pH 7.0) containing ascorbic acid, lactose, and optionally aspartame (Levine et al., Lancet, II: 467 470; 1988). Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10% (w/v).

The biological activity of vector strains is assessed in an appropriate animal model (e.g. mice, rabbits, guinea pigs or Rhesus macaques). Initially, the bacterial vector strains are administered at doses of $10^2$-$10^9$ cfu, and are administered by an appropriate route (e.g. *E. coli*, *Salmonella* and *Shigella* can be given intragastrically or intranasally). The number of doses will vary, depending on the potency of the individual vector strain, and the valency of the encoded recombinant product of interest.

Methods of measurement of immune and other biological responses to encoded products in animal models are well known to those skilled in the art. To measure serum IgG and IgA responses to antigen, sera are collected before and 10, 20, 30, 40, 50, 60, 70, and 80 days after vaccination. About 400-500 µl of blood is collected into individual tubes and allowed to clot by incubating for 4 hr on ice. After centrifugation in a microfuge for five minutes, the sera are transferred to fresh tubes and stored at −80° C. Mucosal IgG and IgA responses to antigens expressed by the genes of interest are determined using fecal pellets and vaginal washes that will be harvested before and at regular intervals after vaccination (Srinivasan et al., Biol. Reprod. 53: 462; 1995); (Staats et al., J. Immunol. 157: 462; 1996). Standard ELISAs are used to quantitate the IgG and IgA responses to an antigen of interest in the sera and mucosal samples (Abacioglu et al., AIDS Res. Hum. Retrovir. 10: 371; 1994); (Pincus et al., AIDS Res. Hum. Retrovir. 12: 1041; 1996). Ovalbumin can be included in each ELISA as a negative control antigen. In addition, each ELISA can include a positive control serum, fecal pellet or vaginal wash sample, as appropriate. The positive control samples are harvested from animals vaccinated intranasally with 10 µg of the antigen expressed by the gene of interest mixed with 10 µg cholera toxin, as described (Yamamoto et al., Proc. Natl. Acad. Sci. 94: 5267; 1997). The end-point titers are calculated by taking the inverse of the last serum dilution that produced an increase in the absorbance at 490 nm that is greater than the mean of the negative control row plus three standard error values.

Cellular immunity may be measured by intracellular cytokine staining (also referred to as intracellular cytokine cytometry) or by ELISPOT (Letsch A. et al., Methods 31:143-49; 2003). Both methods allow the quantitation of antigen-specific immune responses, although ICS also adds the simultaneous capacity to phenotypically characterize antigen-specific CD4+ and CD8+ T-cells. Such assays can assess the numbers of antigen-specific T cells that secrete IL-2, IL-4, IL-5, IL-6, IL-10 and IFN- (Wu et al., AIDS Res. Hum. Retrovir. 13: 1187; 1997). ELISPOT assays are conducted using commercially-available capture and detection mAbs (R&D Systems and Pharmingen), as described (Wu et al., Infect. Immun. 63:4933; 1995) and used previously (Xu-Amano et al., J. Exp. Med. 178:1309; 1993); (Okahashi et al., Infect. Immun. 64:1516; 1996). Each assay includes mitogen (Con A) and ovalbumin controls. The anti-IFN bacterial based delivery system described herein has several advantages over delivery systems without IFN resistant genes. The antigen genes are expressed at higher levels and for longer periods of time, and therefore induce a more vigorous immune response. Bacterial vectors that display efficacy and are non-toxic in animal models are further assessed in clinical trials.

Example 5

Development of a Tuberculosis Vaccine

BCG bacteria are genetically engineered as described herein to contain nucleic acids encoding 1) one or more tuberculosis antigens as passenger genes, and 2) one or more factors that inhibit or interfere with a mammalian host cell type I interferon response. When administered to a mammalian host (e.g. a human), the genetically engineered BCG invade host cells, escape the endosome, and are lysed to release passenger genes to produce the one or more tuberculosis antigens. Further, the BCG also produce the one or more factors that inhibit the host cells IFN response. The factors attenuate the host cell IFN response, which would otherwise decrease the production of the TB antigen(s). As a result, sufficient TB antigen(s) is produced to result in a robust immune response to the TB antigen(s).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of inducing an immune response to one or more antigens of interest in a mammal, comprising:

administering to the mammal a genetically engineered bacterium, comprising:

nucleic acid sequences encoding the one or more antigens of interest; and nucleic acid sequences encoding one or more factors that inhibit a mammalian type I interferon response;

wherein the nucleic acid sequences encoding the one or more antigens of interest are operably linked to a eukaryotic promoter, and the nucleic acid sequences encoding the one or more factors that inhibit a mammalian type I interferon response are operably linked to a eukaryotic promoter or a prokaryotic promoter, and wherein the step of administering is carried out under conditions which allow the genetically engineered bacterium to invade a cell or tissue in the mammal, and which allow the cell or tissue to produce an immune response to the one or more antigens of interest.

2. The method of claim 1, wherein at least one of the antigens of interest is a *Mycobacterium tuberculosis* antigen.

3. The method of claim 1, wherein the nucleic acid sequences encoding the one or more factors that inhibit a mammalian type I interferon response are operably linked to a eukaryotic promoter.

4. The method of claim 1, wherein the nucleic acid sequences encoding the one or more factors that inhibit a mammalian type I interferon response are operably linked to a prokaryotic promoter.

5. The method of claim 1, wherein the nucleic acid sequences encoding the one or more factors that inhibit a mammalian type I interferon response are present on a chromosome of the genetically engineered bacterium.

6. The method of claim 1, wherein one or both of:

i) the nucleic acid sequences encoding the one or more antigens of interest, and ii) the nucleic acid sequences encoding the one or more factors that inhibit a mammalian type I interferon response, are present on a plasmid.

7. The method of claim 1, wherein the one or more factors that inhibit a mammalian type I interferon response are of viral origin.

8. The method of claim 1, wherein the genetically engineered bacterium is a bacterium selected from the group consisting of *Shigella, Listeria, Salmonella*, and Bacille-Calmette-Guerin (BCG).

9. The method of claim 1, wherein the one or more factors that inhibit a mammalian type I interferon response are rotavirus NSP 1 or influenza virus NS1.

10. A method for inducing an immune response to one or more antigens of interest in a mammal, comprising:

administering to the mammal a genetically engineered bacterium, comprising:

one or more genetically engineered nucleic acid sequences coding for a host cell or tissue type 1 interferon (IFN) response suppressor factor; and one or more genetically engineered nucleic acids coding for one or more antigens to which an immune response is desired;

wherein said one or more genetically engineered nucleic acids coding for said one or more antigens to which an immune response is desired are over expressed upon said bacterium invading said host cell or tissue.

11. The method of claim 10, wherein the host cell or tissue type 1 IFN response suppressor factor is rotavirus NSP 1 or influenza virus NS1.

12. The method of claim 10, wherein the one or more antigens to which an immune response is desired are selected from tuberculosis antigens and malaria antigens.

13. The method of claim 10, wherein the one or more antigens to which an immune response is desired is one or more viral antigens.

14. The method of claim 10, wherein the one or more antigens to which an immune response is desired are selected from hormone, enzymes, anticancer agents, and apoptotic factors.

15. The method of claim 10, wherein the host cell or tissue type 1 IFN response suppressor factor is selected from the group consisting of rotavirus NSP1, influenza virus NS1, ectromelia virus C12R protein, hepatitis C virus NS3/4A protease, vaccinia virus vIFN-α/β Rc protein, adenovirus E1A protein, C proteins of paramyxoviruses, and human papillomavirus (HPV) E6 oncoprotein.

16. The method of claim 13, wherein the one or more viral antigens is a rotavirus viral antigen, influenza virus viral antigen, ectromelia virus viral antigen, hepatitis virus viral antigen, vaccinia virus viral antigen, adenovirus viral antigen, paramyxovirus viral antigen, HPV viral antigen, HIV viral antigen, HTLV viral antigen, enterovirus viral antigen, herpesvirus viral antigen, EEE viral antigen, VEE viral antigen, West Nile virus viral antigen, Norwalk virus viral antigen, parvovirus viral antigen, dengue virus, viral antigen or hemorrhagic fever virus viral antigen.

\* \* \* \* \*